United States Patent
Lugt et al.

(10) Patent No.: US 12,392,702 B2
(45) Date of Patent: Aug. 19, 2025

(54) SYSTEM FOR DETERMINING RHEOLOGICAL PROPERTIES OF GREASE AND ASSOCIATED METHOD

(71) Applicant: Aktiebolaget SKF, Gothenburg (SE)

(72) Inventors: Pieter Martin Lugt, TA Vianen (NL); Robert Jan Meijer, HZ Delden (NL)

(73) Assignee: Aktiebolaget SKF, Gothenburg (SE)

( * ) Notice: Subject to any disclaimer, the term of this patent is extended or adjusted under 35 U.S.C. 154(b) by 362 days.

(21) Appl. No.: 17/836,045

(22) Filed: Jun. 9, 2022

(65) Prior Publication Data

US 2022/0397505 A1  Dec. 15, 2022

(30) Foreign Application Priority Data

Jun. 15, 2021  (DE) .............................. 102021206088

(51) Int. Cl.
| | |
|---|---|
| *G01N 11/10* | (2006.01) |
| *G01F 1/05* | (2006.01) |
| *G01N 33/28* | (2006.01) |

(52) U.S. Cl.
CPC ............... *G01N 11/10* (2013.01); *G01F 1/05* (2013.01); *G01N 33/28* (2013.01)

(58) Field of Classification Search
CPC ........... G01N 11/10; G01N 33/28; G01F 1/05
See application file for complete search history.

(56) References Cited

U.S. PATENT DOCUMENTS

| | | | | |
|---|---|---|---|---|
| 4,343,190 A | * | 8/1982 | Danko ................. | G01N 11/165 73/54.39 |
| 8,549,930 B2 | * | 10/2013 | Wurzbach ............. | G01N 11/08 73/861.52 |
| 2018/0292465 A1 | * | 10/2018 | Osara ................. | G01N 33/2888 |

FOREIGN PATENT DOCUMENTS

| | | | | | |
|---|---|---|---|---|---|
| CN | 203132952 U | * | 8/2013 | | |
| CN | 108613899 A | * | 10/2018 | ............. | G01N 11/00 |
| CN | 110107591 A | * | 8/2019 | ............ | F16C 19/522 |

\* cited by examiner

*Primary Examiner* — Lisa M Caputo
*Assistant Examiner* — Nyla Gavia
(74) *Attorney, Agent, or Firm* — GARCIA-ZAMOR INTELLECTUAL PROPERTY LAW, LLC; Ruy Garcia-Zamor

(57) ABSTRACT

System for determining rheological properties of grease, includes a grease worker having a cylinder intended to contain the grease and a piston intended to move inside the cylinder in a first direction and in a second opposite direction and provided with holes. The grease worker further including a seal provided between the piston and the cylinder, force for measuring the force required to push the grease through the holes of the piston is measured an electrical motor and an eccentrical connection transforming the rotating motion of the motor in a translation motion pushes the grease thought the holes, a thermocouple for measuring a temperature of the cylinder, a fan and a heater for regulating temperature for maintaining constant the measured temperature at a predetermined temperature, and a computing unit configured to determine at least one rheological property of the grease from the measured forces and from the seal friction.

8 Claims, 5 Drawing Sheets

SYSTEM FOR DETERMINING RHEOLOGICAL PROPERTIES OF GREASE AND ASSOCIATED METHOD

CROSS-REFERENCE TO RELATED APPLICATIONS

This application claims priority to German Patent Application no. 102021206088.9, filed Jun. 15, 2021, the contents of which is fully incorporated herein by reference.

TECHNICAL FIELD OF THE INVENTION

The present invention is directed to a method and a system for determining rheological properties of grease. More particularly, the invention deals with determining rheological properties of grease without a rheometer.

BACKGROUND OF THE INVENTION

The specifications of lubricating greases are measured according to standards.

According to the standards, the specifications of grease like the consistency is measured before and after an aging procedure in a grease worker giving few information about the specifications.

However, the follow-up of the evolution of rheological properties of grease during aging of grease is relevant.

The present invention intends to propose a method and a system to follow-up the evolution of rheological properties of grease during aging of grease.

According to an aspect, a method for determining rheological properties of grease is proposed.

The method comprises:
(a) moving a piston in a first direction inside a cylinder containing the grease to push the grease through holes of the piston, a seal being provided between the piston and the cylinder,
(b) measuring the force required to push the grease through the holes of the piston,
(c) moving the piston in a second direction opposite to the first direction inside the cylinder,
(d) measuring the temperature of the cylinder
(e) maintaining the temperature of the cylinder at a predetermined temperature,
(f) repeating steps (a), (b) and (c) during a predetermined number to obtain a set of measured forces, and
(g) determining at least one rheological property from the measured forces and from the seal friction.

Such method permits to calculate rheological properties of grease from the energy transferred to the grease.

The evolution of rheological properties is monitored in-situ eliminating the need to do separate measurements using a rheometer to obtain these properties.

The monitoring in-situ of the grease eliminates using new grease samples for each measurement leading to an increase in reliability.

Preferably, the step (g) of determining at least one rheological property comprises determining the total energy density transferred to the grease comprising:
filtering the set of measured forces,
modelling the piston velocity according the filtered set of measured forces
determining the seal friction according to predetermined fitting parameters and to the piston velocity
determining a second set of forces from the filtered set of measured forces and the seal friction,
calculating the instantaneous power density transferred to the grease according to the second set of forces, the velocity model of the piston and the volume of grease inside the cylinder
calculating the average power density transferred to the grease for each piston stroke between the first and second directions of the cylinder from the instantaneous power density, and
calculating the total energy density by summing the instantaneous power density or by integrating the instantaneous power density.

Advantageously, the step (g) of determining at least one rheological property comprises determining a power law fluid equation linking the flow rate and pressure drop of the grease flowing through the holes, dimensional parameters and behaviour parameters.

Preferably, determining the power law fluid equation comprises:
determining the flow rate and the total pressure drop of the grease flowing through the holes of the piston according to the diameter of the piston, the number of holes, the velocity model of the piston, the second set of forces and the inner diameter of the cylinder for a predetermined number of piston strokes, and
adjusting the behaviour parameters comprising a flow consistency parameter and a flow behaviour index so that the power law fluid equation fits the flow rate and the total pressure drop for the predetermined number of piston strokes.

Advantageously, the method comprises determining the shear rate of the grease according to the diameter of the holes of the piston, the flow rate and the adjusted flow behaviour index.

Preferably, the method comprises determining the viscosity of the grease according to the shear rate of the grease, the flow consistency parameter and the flow behaviour index.

Advantageously, the power law fluid equation is equal to power law fluid equation for a pipe flow through a very short section of a circular pipe.

Preferably, the method comprises an empirical determination of the predetermined fitting parameters during an identification phase.

According to another aspect, a system for determining rheological properties of grease is proposed.

The system comprises:
a grease worker comprising a cylinder intended to contain the grease and a piston intended to move inside the cylinder in a first direction and in a second opposite direction and provided with holes, the grease worker further comprising a seal provided between the piston and the cylinder,
force measuring means for measuring the force required to push the grease through the holes of the piston,
moving means for moving the piston in the first direction and in the second direction,
temperature measuring means for measuring a temperature of the cylinder
temperature regulating means for maintaining constant the measured temperature at a predetermined temperature, and
a computing unit configured to determine at least one rheological property of the grease from the measured forces and from the seal friction.

The system forms a cheap rheometer.

BRIEF DESCRIPTION OF THE DRAWINGS

At least one of the embodiments of the present invention is accurately represented by this application's drawings which are relied on to illustrate such embodiment(s) to scale and the drawings are relied on to illustrate the relative size, proportions, and positioning of the individual components of the present invention accurately relative to each other and relative to the overall embodiment(s). Those of ordinary skill in the art will appreciate from this disclosure that the present invention is not limited to the scaled drawings and that the illustrated proportions, scale, and relative positioning can be varied without departing from the scope of the present invention as set forth in the broadest descriptions set forth in any portion of the originally filed specification and/or drawings. The present invention and its advantages will be better understood by studying the detailed description of specific embodiments given by way of non-limiting examples and illustrated by the appended drawings on which.

DETAILED DESCRIPTION OF THE INVENTION

Figure 1:
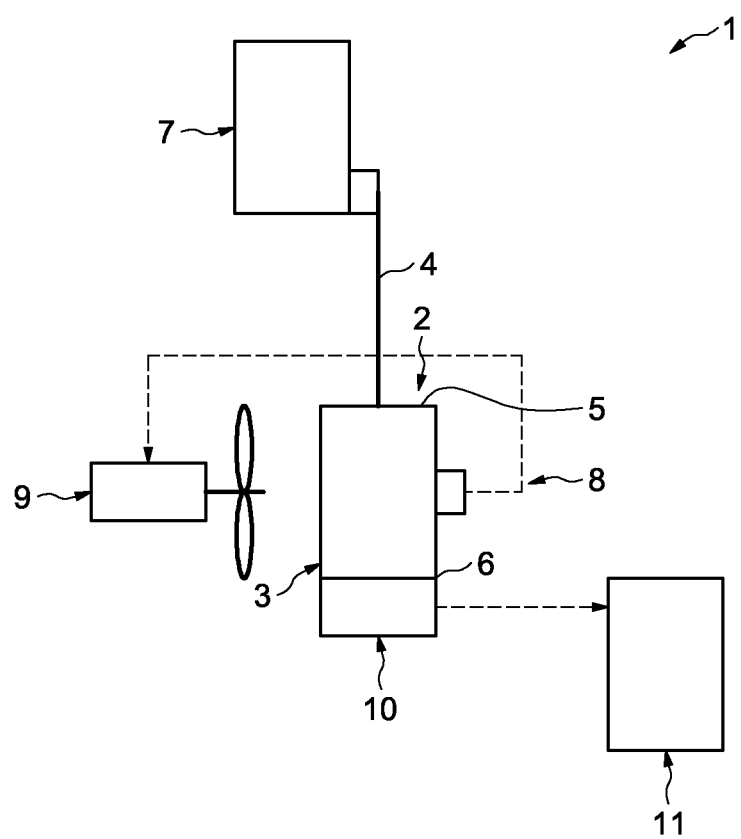
FIG. 1 illustrates schematically a system for determining rheological properties of grease according to an example of the invention.

Those of ordinary skill in the art will appreciate from this disclosure that when a range is provided such as (for example) an angle/distance/number/weight/volume/spacing being between one (1 of the appropriate unit) and ten (10 of the appropriate units) that specific support is provided by the specification to identify any number within the range as being disclosed for use with a preferred embodiment. For example, the recitation of a percentage of copper between one percent (1%) and twenty percent (20%) provides specific support for a preferred embodiment having two point three percent (2.3%) copper even if not separately listed herein and thus provides support for claiming a preferred embodiment having two point three percent (2.3%) copper. By way of an additional example, a recitation in the claims and/or in portions of an element moving along an arcuate path by at least twenty) (20°) degrees, provides specific literal support for any angle greater than twenty) (20°) degrees, such as twenty-three) (23°) degrees, thirty) (30°) degrees, thirty-three-point five) (33.5°) degrees, forty-five) (45°) degrees, fifty-two) (52°) degrees, or the like and thus provides support for claiming a preferred embodiment with the element moving along the arcuate path thirty-three-point five) (33.5°) degrees. Reference is made to FIG. 1 which represents a system for determining rheological properties of grease.

The system 1 comprises a grease worker 2 comprising a cylinder 3 and a piston 4 moving inside the cylinder 3. The grease worker 2 further comprises a seal 16 (represented on FIG. 2) interposed between the cylinder 3 and the piston 4. The seal 16 is secured to the cylinder 3 and comes into friction contact with the piston 4.

The cylinder 3 comprises a first end 5 in which the piston 4 is inserted in the cylinder 3, and a closed end 6 opposite to the first.

The first end 5 and the closed end 6 define a chamber.

The grease GR is disposed inside the cylinder 3 to completely fill up the chamber between the first end 5 and the closed end 6 of the cylinder 3 to avoid that air is trapped in the chamber.

The trapped air may disturb the determination of rheological properties of grease.

The system further comprises moving means 7 for moving the piston 4 in a first direction inside the cylinder 3 and in a second direction opposite to the first direction.

The first direction is oriented so that the piston 4 translates towards the closed end 6.

The moving means 7 may comprise an electrical motor and an eccentrical connection transforming the rotating motion of the motor in a translation motion so that the grease OR flows thought the holes of the piston 4 when the piston 4 moves from the first end 5 to the second end 6.

The system 1 further comprises temperature measuring means 8 and temperature regulating means 9.

The temperature regulating means 9 may comprise cooling means to cool the cylinder 3 and heating means to heat the cylinder 3.

The temperature measuring means 8 measure the temperature of the cylinder 3. The temperature measuring means 8 comprise for example a thermocouple disposed on the external surface of the cylinder 3.

The temperature regulating means 9 maintain constant the temperature measured by the temperature measuring means 8 at a predetermined temperature, so that any change in rheological parameters of the grease OR is caused by aging and not by a change in temperature.

The cooling means may for example comprise a fan and the heating means may for example comprise a heater.

The system 1 further comprises force measuring means 10, and a computing unit 11 connected to the force measuring means 10.

The force measuring means 10 measure forces required to push the grease (JR in the chamber through holes 13 of the piston 4.

The computing unit 11 determines at least one rheological property of the grease OR from the measured forces by the force measuring means 10 and from the seal friction of the seal of the cylinder 3.

Figure 2:
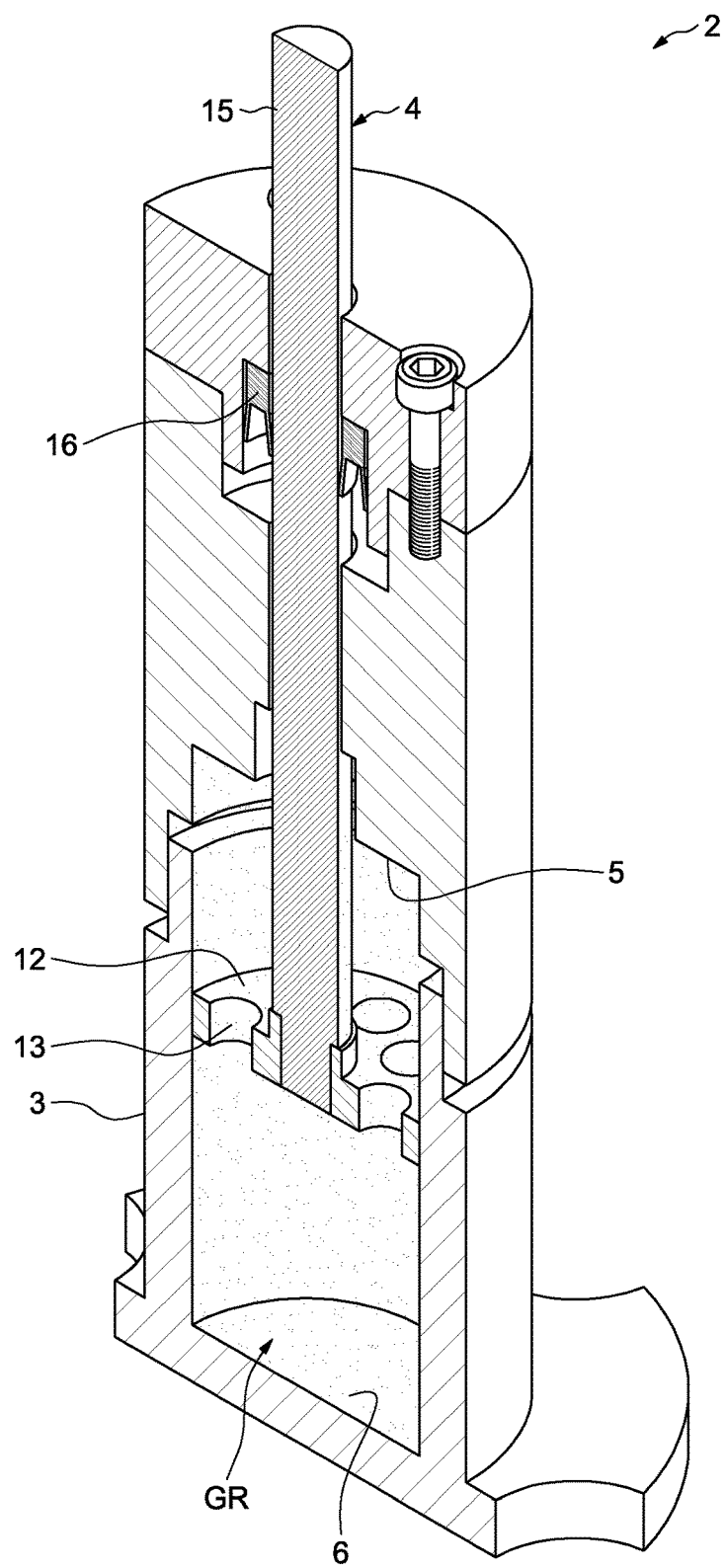
FIG. 2 is a longitudinal section of a grease worker according to an example of the invention.
Figure 3:
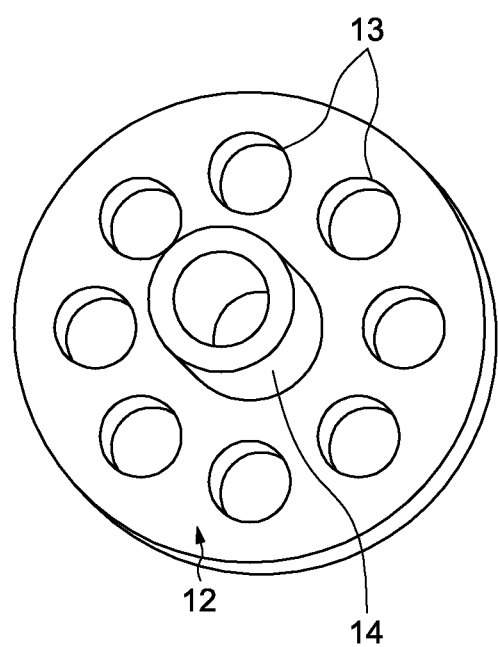
FIG. 3 is a perspective view of a piston of the grease worker of FIG. 2.

As shown on FIGS. 2 and 3, the piston 4 comprises a plate 12 provided with holes 13 of the piston 4, and a rod or shaft 15 supporting the plate. The seal 16 comes into friction contact with the shaft 15 of the piston. The seal 16 radially comes into friction contact with the shaft 15.

The holes 13 extend axially through the thickness of the plate 12. The holes 13 are through holes. The holes 13 are identical. The holes 13 are regularly arranged on the piston plate 12 along the same diameter.

The piston plate 12 further comprises a thread central hole 14 into which is secured the shaft 15.

Figure 4:
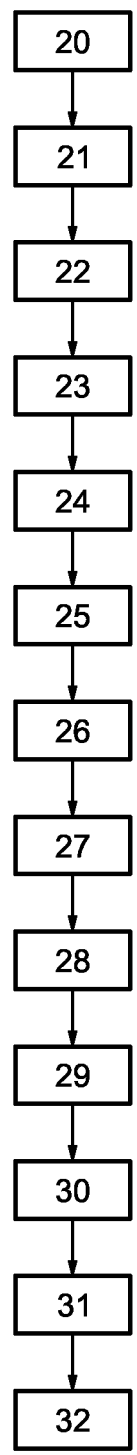
FIG. 4 illustrates a method for determining rheological properties of grease according to an example of the invention.

FIG. 4 illustrates an example of a method for determining rheological properties of grease GR from the system 1.

In step 20, the moving means 7 move the piston 4 inside the chamber of the cylinder 3 in the first direction so that grease OR flows through the holes 13 of the piston 4 and then in the second direction for a predetermined number N, each motion in the first direction and in the second direction forming a piston cycle or piston stroke, the predetermined number N being the number of piston cycles.

The computing unit 11 collects the values measured by the measuring means 10 for each piston cycle to determine a set of measured forces F1 during a duration $T_{exp}$.

During the collecting of the set of forces F1, the cooling means 9 commanded by the temperature measuring means 8 maintain the temperature of the cylinder 3 constant equal to the ambient temperature of the system 1.

Figure 5:
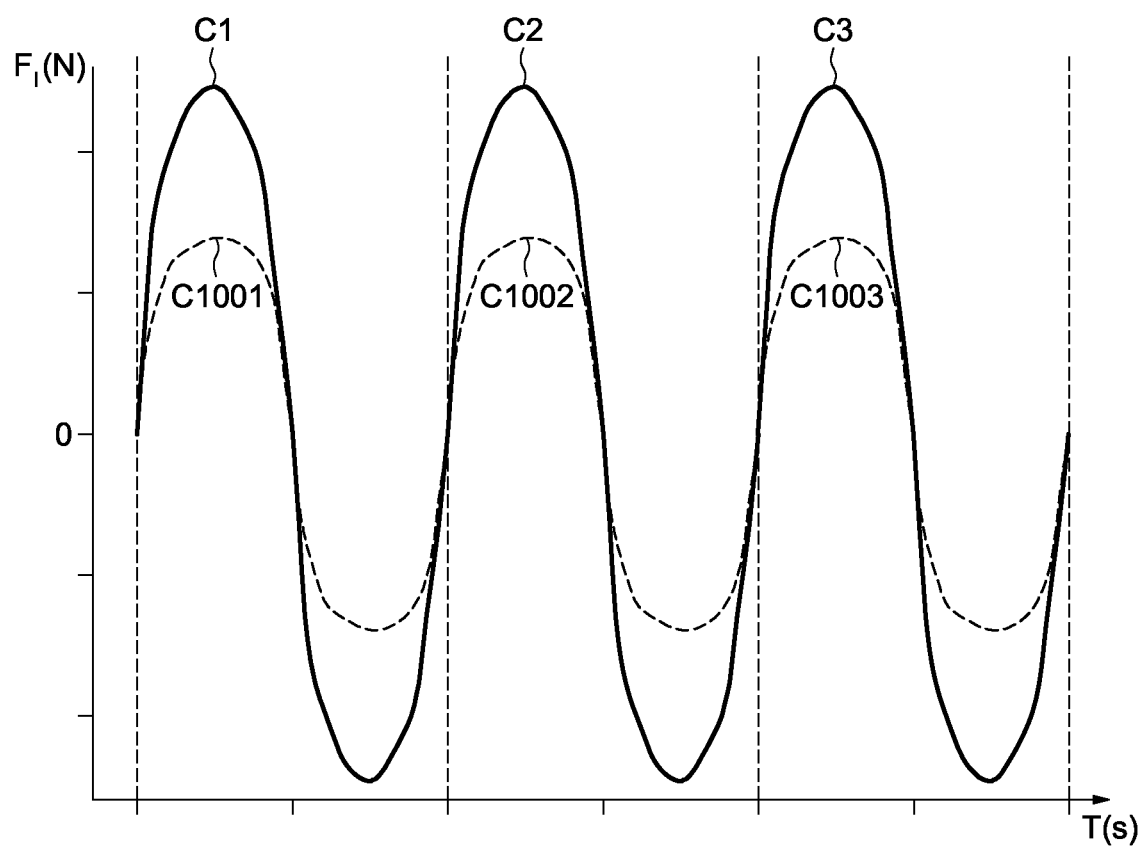
FIG. 5 illustrates an example for measured forces measured by measuring means over the time.

FIG. 5 illustrates an example for measured forces F1 measured by the measuring means 10 over the time T.

Curves C1, C2 and C3 represent the evolution of the measured forces F1 for the first three cycles after the introduction of fresh grease GR in the cylinder 3, and curves C1001, C1002 and C1003 represent the evolution of the measured forces $F_1$ for the 1001, 1002 and 1003 cycles after the introduction of fresh grease OR in the cylinder 3.

Referring once again to FIG. 4, n steps 21 to 27, the computing unit 11 determines the total energy density transferred to the grease by the grease worker 2.

In step 21, the set of measured forces F1 is filtered to remove the fundamental frequency of the measured values of forces F1 by a high-pass filter.

The high-pass filter may be implemented by the computing unit 11 and has for example a cut-off frequency of 0.5 Hz.

In step 22, the computing unit 11 models the piston velocity v of the piston 4 according to the filtered set of forces $F_{F1}$.

The velocity is model with:

$$v(t) = 2\cdot\pi \cdot f \cdot \hat{s} \cdot \sin(2\cdot\pi \cdot f \cdot t) \tag{1}$$

where f is the piston cycle frequency equal to 1 Hz according to the standards, t is the time and ŝ is the maximum amplitude of the piston 4 inside the cylinder 3.

In step 23, the computing unit 11 determines a model of the seal friction $F_s$ generated by the seal 16 on the piston 4 according to predetermined fitting parameters $a_0$, $a_1$, $a_2$, $a_3$ and $a_4$, and the piston velocity v:

$$Fs(v,t) = (a_0 e^{a_1 t} + a_2)\sin(a_3 \tanh(a_4 v)) \tag{2}$$

The predetermined fitting parameters $a_0$, $a_1$, $a_2$, $a_3$ and $a_4$ are determined empirically during an identification phase of the seal 16.

In step 24, the computing unit 11 determines a second set of forces $F_g$. The seal friction force Fs of equation (2) is subtracted from the filtered set of forces $F_{F1}$ to get the second set of forces $F_g$ equal to the forces required to push the grease through the holes 13 of the piston plate 12.

In step 25, the computing unit 11 calculates the instantaneous power density transferred to the grease equal to the instantaneous power density $P_g$, required to push the grease through the holes 13:

$$P_g(t) = \frac{F_g v}{V_{gw}} \tag{3}$$

where is the internal volume of the cylinder 3.

The two first piston cycles and the two last piston cycles are excluded to calculate the instantaneous power density $P_g$ to exclude running in and running out effects.

In step 26, the average power density $P_g$ for e piston cycle $n_s$ is calculated by the computing unit 11:

$$P_s(n_s) = \frac{1}{t_{i+1} - t_i} \int_{t_i}^{t_{i+1}} P_g(t) dt \tag{4}$$

where each piston cycle $n_s$ starts when the velocity v is equal to zero at time $t_i$ and ends after a full cycle at time $t_{i+1}$.

In step 27, the computing unit 11 calculates the total energy density $E_g$ by summing the energy density Es for each piston cycle $n_s$:

$$E_g = \Sigma_{n_s=1}^{N} E_s(n_s) \tag{5}$$

where:

$$E_s(n_s) = \int_{t_i}^{t_{i+1}} P_g(t) dt \tag{6}$$

In another embodiment, replacing steps 26 and 27, the computing unit 11 integrates the instantaneous power density $P_g$ over the measurement duration $T_{exp}$ to calculate the total energy density $E_g$:

$$E_g = \int_o^{T_{exp}} P_g(t) dt \tag{7}$$

In steps 28 to 29, the computing unit 11 determines a power law fluid equation linking the flow rate Q and the pressure drop ΔPp of the grease flowing through the holes 13, dimensional parameters and behaviour parameters the total energy density.

The dimensional parameters comprise:
R the hole radius of the holes 13,
L the thickness of the piston plate 12,
$d_p$ the diameter of the piston 4,
$n_h$ the number of holes 13 of the piston 4, and
$d_{gw}$ the inner diameter of the cylinder 4

As the flow of grease OR through the holes 13 of the piston plate 12 can be considered as a pipe flow through a very short section of a circular pipe, the power law fluid equation is equal to:

$$\Delta P_p = \frac{2KL}{R}\left(\frac{Q(3n+1)}{\pi R^3 n}\right)^n \tag{8}$$

where the behaviour parameters comprise the parameters K and n, K being the flow consistency and n being the flow behaviour index.

The behaviour parameters K and n are unknown.

In step 28, the computing unit 11 determines the flow rate Q and the total pressure drop $\Delta P_g$ of the grease OR flowing through the holes 13:

$$Q = \frac{1}{4}\frac{\pi d_p^2 v}{n_h} \tag{9}$$

$$\Delta P_g = \frac{4F_g}{\pi d_g^2 w} \tag{10}$$

in step 29, the computing unit 11 determines a second expression of the total pressure drop $\Delta P_g$ of the grease OR flowing through the holes 13 from equation (8) to take into account the pressure loss of the grease flowing in the holes 13 and out the holes 13, the part of the holes in the thickness of the piston plate being consider as short pipes:

$$\Delta P_q = \Delta P_p\left[1 + 2\left(\frac{0.6D}{2L}\frac{3(3n+1)^2}{2(2n+1)(5n+3)}\right)\right] \tag{11}$$

in step 30, the computing unit 11 adjusts the flow consistency parameter K and the flow behaviour index n so that the power law fluid equation (8) fits the flow rate Q and the total pressure drop $\Delta P_g$ for a predetermined number of piston cycles.

In step 31, the computing unit 11 determines the shear rate y of the grease GR:

$$\dot{y} = \frac{2Q(3n+1)}{\pi R^3 n\left(2 + \frac{1}{n}\right)} \quad (12)$$

In step 32, the computing unit 11 determines the viscosity η of the grease GR:

$$\eta = K\dot{y}^{n-1} \quad (13)$$

The presented method permits to calculate rheological properties of grease from the energy transferred to the grease.

The evolution of rheological properties is monitored in-situ eliminating the need to do separate measurements using a rheometer tip obtain these properties.

Further, monitoring the grease evolution in-situ gives the advantage that it is no longer needed to use new grease samples for each measurement, leading to an increase in reliability.

Further, the presented method can also be used to measure the rheological properties of a (semi-)fluid, such as grease, without working the grease. In addition, the system 1 also forms a cheap rheometer.

The invention claimed is:

1. A method for determining rheological properties of grease, comprising:
   (a) moving a piston in a first direction inside a cylinder containing the grease to push the grease through holes of the piston, a seal being provided between the piston and the cylinder,
   (b) measuring the force required to push the grease through the holes of the piston,
   (c) moving the piston in a second direction opposite to the first direction inside the cylinder,
   (d) measuring the temperature of the cylinder,
   (e) maintaining the temperature of the cylinder at a predetermined temperature,
   (f) repeating steps (a), (b) and (c) during a predetermined number to obtain a set of measured forces, and
   (g) determining at least one rheological property and the total energy density transferred to the grease, the at least one rheological property being determined from the measured forces and from the seal friction, the total energy density being determined by the following steps:
   filtering the set of measured forces,
   modelling the piston velocity according to the filtered set of measured forces,
   determining the seal friction according to predetermined fitting parameters and to the piston velocity,
   determining a second set of forces from the filtered set of measured forces and the seal friction,
   calculating the instantaneous power density transferred to the grease according to the second set of forces, the velocity model of the piston and the volume of grease inside the cylinder,
   calculating the average power density transferred to the grease for each piston stroke between the first and second directions of the cylinder from the instantaneous power density, and
   calculating the total energy density by summing the instantaneous power density or by integrating the instantaneous power density.

2. The method according to claim 1, wherein the step (g) of determining at least one rheological property comprises determining a power law fluid equation linking the flow rate and pressure drop of the grease flowing through the holes, dimensional parameters and behaviour parameters.

3. The method according to claim 2, wherein determining the power law fluid equation comprises:
   determining the flow rate and the total pressure drop of the grease flowing through the holes of the piston according to the diameter of the piston, the number of holes, the velocity model of the piston, the second set of forces and the inner diameter of the cylinder for a predetermined number of piston cycles, and
   adjusting the behaviour parameters comprising a flow consistency parameter and a flow behaviour index so that the power law fluid equation fits the flow rate and the total pressure drop for the predetermined number of piston strokes.

4. The method according to claim 3, comprising determining the shear rate of the grease according to the diameter of the holes of the piston, the flow rate and the adjusted flow behaviour index.

5. The method according to claim 4, comprising determining the viscosity of the grease according to the shear rate of the grease, the flow consistency parameter and the flow behaviour index.

6. The method according to claim 2, wherein the power law fluid equation is equal to power law fluid equation for a pipe flow through a very short section of a circular pipe.

7. The method according to claim 1, comprising an empirical determination of the predetermined fitting parameters during an identification phase.

8. A system for determining rheological properties of grease, comprising:
   a grease worker comprising a cylinder intended to contain the grease and a piston intended to move inside the cylinder in a first direction and in a second opposite direction and provided with holes, the grease worker further comprising a seal provided between the piston and the cylinder,
   force measuring means for measuring directly the force of the piston required to push the grease through the holes of the piston by:
   modelling the piston velocity according to the filtered set of measured forces,
   determining the seal friction according to predetermined fitting parameters and to the piston velocity,
   determining a second set of forces from the filtered set of measured forces and the seal friction,
   calculating the instantaneous power density transferred to the grease according to the second set of forces, the velocity model of the piston and the volume of grease inside the cylinder,
   calculating the average power density transferred to the grease for each piston stroke between the first and second directions of the cylinder from the instantaneous power density, and
   calculating the total energy density by summing the instantaneous power density or by integrating the instantaneous power density,
   moving means for moving the piston in the first direction and in the second direction,
   temperature measuring means for measuring a temperature of the cylinder,
   temperature regulating means for maintaining constant the measured temperature at a predetermined temperature, and a computing unit configured to determine at least one rheological property of the grease from the filtering the set of measured forces.

* * * * *